United States Patent [19]

Botterbusch et al.

[11] Patent Number: 5,004,456
[45] Date of Patent: Apr. 2, 1991

[54] IN-DWELLING CATHETER

[75] Inventors: Carl N. Botterbusch, Reading; Paul L. Frankhouser, Wyommissing, both of Pa.

[73] Assignee: Arrow International Investment Corporation, Wilmington, Del.

[21] Appl. No.: 321,768

[22] Filed: Mar. 10, 1989

[51] Int. Cl.$^5$ .................... A61M 25/00; A61M 25/06
[52] U.S. Cl. ...................... 604/53; 604/158; 604/280
[58] Field of Search .................. 604/280–284, 604/264, 158, 164, 53; 128/656, 658

[56] References Cited

U.S. PATENT DOCUMENTS

| 4,385,635 | 5/1983 | Ruiz | 604/280 |
| 4,500,313 | 2/1985 | Young | 604/280 |
| 4,563,181 | 1/1986 | Wijayarathna | 604/650 |

Primary Examiner—Stephen C. Pellegrino
Attorney, Agent, or Firm—Charles H. Lindrooth; Peter J. Cronk

[57] ABSTRACT

A catheter intended for the administration of an anesthetic into a body space and methods of use such as introduction within the interpleural space are disclosed. According to the disclosure, the catheter is constructed so that only a soft distal portion resides within the body space. A relatively stiff portion joined to the relatively soft portion is intended to extend from the relatively soft portion through the dense body tissue to the proximal end of the catheter. A bio-compatible resin providing a softness of about 80A to 100A Rockwell is used for the relatively soft distal portion. A bio-compatible resin providing a catheter portion having a durometer value of about 65D to about 75D Rockwell is used for the relatively stiff portion. The relatively soft portion avoids damage to the delicate body tissue bounding the space whereas the relatively stiff portion resists kinking or collapse, both within the relatively stiff body tissue and outside the body. Spaced apart reference markings are provided on the relatively stiff portion of the catheter in position to provide a visual indication of the amount of the relatively soft distal portion that is within the body space.

11 Claims, 1 Drawing Sheet

IN-DWELLING CATHETER

FIELD OF THE INVENTION

This invention relates to catheters intended for the administration of local anesthetic into a body space, more particularly to a catheter designed to avoid trauma to delicate body tissue within the space while remaining in place for prolonged periods of time.

BACKGROUND OF THE INVENTION

Catheters of the kind referred to are particularly useful for the administration of medicaments, more particularly for the continuous administration of anesthesia within the epidural or intra-pleural (interpleural) spaces. In each application, the space involved is relatively long and narrow and is relatively inaccessible except in a direction which is at an angle relative to the long axis of the space. In each instance, nerves and relatively delicate body tissues are involved which are subject to trauma, producing paresthesia and in some cases considerable discomfort and permanent injury due to disturbance of the relatively delicate tissue bordering the space. In extreme cases, puncture, irritation or erosion of the tissue can result.

In the use of intra-vascular catheters, relatively short, soft distal tips for catheters for venous and arterial use have recently come into use as a means of avoiding vessel puncture and the dislodgment of plaque with the vessel. In these applications, substantially all of the catheter dwelling within the vessel must be relatively stiff due to the need to guide and turn the catheter tip within the vessel. Because of this limitation, the soft tip employed on an intra-vascular catheter has at most been about one to one and one half centimeters in length. Catheters of this type have not been recognized or considered to be adaptable for use within the epidural or intrapleural spaces because the relativelY stiff material comprising the major part of the catheter may damage the delicate tissues within the space. Further, the restlessness of patients to whom anesthesia is administered by intra-pleural and epidural techniques increases the risk that the soft tip will become separated from the body of the catheter, particularly since the catheter may reside within the space over a period of many days or even weeks.

SUMMARY OF THE INVENTION

With the foregoing in view, the present invention provides a catheter which has an elongated soft distal section intended to reside within a body cavity and a substantially stiffer, kinkresistant, proximal section extending proximally from a junction with the distal section. Preferably the junction with the distal section comprises a relatively short intermediate section in which polymers of the distal and proximal portions are bonded by the application of sufficient heat to cause the materials to freely flow together in a large bond area thereby integrally joining the softer distal end portion to the stiffer proximal portion. Preferably the stiffer proximal portion is provided with one or more indicator markings spaced from the tip to enable the anesthesiologist to make certain that only the relatively soft distal portion is within the body space and that the relatively stiff section is within the relatively dense tissue proximally of the body space and outside the body. Preferably the soft portion is long enough so that it extends into the relatively dense tissue by a centimeter or two so as to provide a relatively soft buffer zone. Since the requirement for anesthetic administration (either intermittently or continuously) may remain for a prolonged period extending as long as a week or more, the relative stiffness of the section of catheter proximally of the soft portion provides resistance to kinking or collapsing and interruption of flow caused by patient restlessness. To insure that the tip will not become separated from the remainder of the catheter, care must be taken that a strong bond exists between the relatively soft tip portion and the relatively stiff portion. Preferably this is accomplished by abutting the two sections together and applying heat sufficient to effect a flowing together of the relatively stiff and the relatively soft resins within a relatively short transition zone of approximatelY one sixteenth of an inch in length. Although longer transition zones may be provided, the transition zone must not be too long, i.e. two to three centimeters, since there is a risk that it would project outside the body when the tip is positioned.

Preferably, the relatively stiff portion of the catheter is formed of a polyurethane resin having a durometer reading of about 68D Rockwell. Resins ranging in stiffness from about 65D to about 75D may be employed. For certain procedures an elongated stiffening wire stylet may be provided for use in the introduction of the catheter. If the stylet is employed, its distal end should not enter the relatively soft distal end portion.

In a preferred mode of use of the catheter for intrapleural administration of anesthesia, a skin wheal is raised at the chosen puncture site and a small skin nick made to facilitate penetration. A curved-tip needle such as a 17 gauge needle of the Husted type with stylet inserted is introduced at a 30 degree to 40 degree angle to the skin into the intercostal space just above the upper edge of the lower rib. The needle is advanced in the medial direction with the cutting edge upwardly after perforation of the caudal intercostal membrane, which can be identified bY the distinct resistance it offers. Upon removal of the needle stylet, a syringe is attached to the needle with the plunger retracted between about 2–4 centimeters. The needle is advanced slowly. When the parietal pleura is perforated the syringe plunger will begin to return to the non-retracted position due to the negative pressure within the pleural space. The syringe is then removed and the distal tip of the catheter quickly threaded through the needle. When the tip of the catheter reaches the curved point of the needle, a slight increase in pressure is felt which indicates that the catheter is about to enter the pleura. At that point a first reference mark on the catheter will substantially coincide with the needle hub. Subsequent pressure to advance the catheter should be minimal. When a more remote reference mark coincides with the needle hub, the catheter has been inserted 5 centimeters into the pleura. Thereafter, the needle is removed while maintaining the catheter in place; the catheter is then coiled into a strain loop and fixed in place, a syringe is attached in the usual manner and the anesthetic administered as required.

A similar procedure is employed for catheterization of the epidural space although a stiffening stylet is preferably fitted within the lumen of the catheter, the stylet distal tip terminating short of the softer distal portion. As is recognized in the art, in the use of epidural catheters, the hanging drop method or the loss of resistance technique are employed in determining penetration of the dura.

IN DRAWINGS

DETAILED DESCRIPTION OF PREFERRED EMBODIMENT

Figure 1:
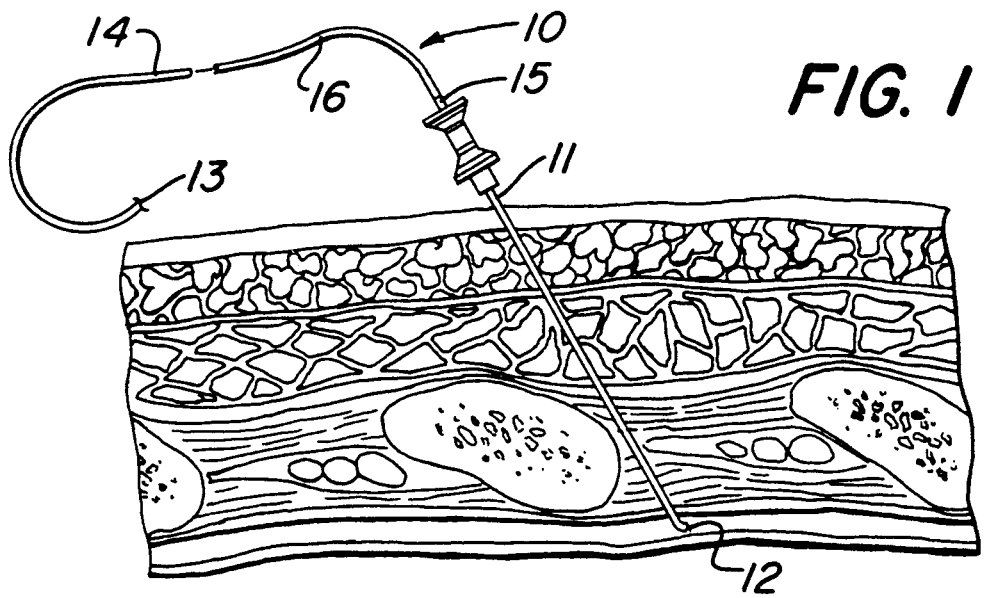
FIG. 1 shows a catheter formed in accordance with the invention, as inserted through a hollow bevelled tip needle and about to enter the pleural space.

With reference to the drawings, a catheter is shown by way of example as being introduced into the pleural space for administration of anesthetic, such as for the administration of bupivacaine solution for pain relief in a patient with multiple rib injuries. Other procedures, such as anesthetic administration within the epidural space, are also contemplated with the present invention. The catheter formed according to the teachings of the invention is shown at 10 and is formed of biocompatible, radio opaque resin materials. Preferably the catheter is about 90 centimeters in length and is about 19 gauge in diameter. Such a catheter is illustrated as being introduced through a 17 gauge curved-tip needle 11.

Catheter 10 is of substantially uniform outer diameter and has a single lumen extending lengthwise thereof to an exit port 12 in the distal tip through which anesthetic solution or other medication is adapted to be administered. Additional lumens may be provided if required. The proximal end of the catheter 13 is initially not provided with any fitting so as to allow for complete withdrawal of the needle over the catheter and removal once the catheter is in place. After the needle is withdrawn and removed, the proximal end of the catheter can then be fitted into a catheter-syringe adapter and a syringe attached for injection of the anesthetic as required.

According to the invention, the catheter 10 is comprised of a relatively long distal tip section 13, formed of a biocompatible resin. A critical feature of the tip portion is that the tip be of relatively soft material throughout the length intended to reside within the body space so as to avoid irritation and damage to delicate tissue. Preferably a biocompatible resin providing a tip section having a durometer reading of about 93A Rockwell is employed. A suitable biocompatible resin is an aliphatic polyurethane manufactured by Thermedics under the trademark TECOFLEX or a similar resin of Dow Chemical Company. Aromatic polyurethanes such as Tellethane, also from Dow Chemical Company, may be employed. From the biocompatible resins specified above, relatively soft resins having a specified durometer value of from 8OA to 1OOA Rockwell may be employed. The tip section should preferably be at least 4 centimeters up to about 8 centimeters in length, although the length may vary in practice. An insertion length of about 5 centimeters in length for administration of anesthetic within the pleural or epidermal spaces with an extra centimeter or two to insure that only the soft portion is within the space has proven to be satisfactory.

The relatively soft distal portion 13 is joined to a relatively rigid proximal portion 14 which extends to the proximal end of the catheter. Preferably the relatively rigid 14 portion is also formed of a bio-compatible polyurethane resin. Excellent results are obtainable utilizing a aliphatic polyurethane resin as identified above and capable of producing a catheter material having a durometer reading of about 68D Rockwell. A material of this stiffness has proved to be sufficiently resistant to kinking and collapse under normal conditions of use so that closure of the lumen by kinking or by pressure from the relatively dense bodY tissue in which this portion of the catheter is to reside is avoided. Others of the resins noted above having a Rockwell value of 65D to 75D may be employed. The stiffer out-dwelling portion also resists kinking or collapsing outside of the body, which is especially critical when the catheter is used in the epidural technique where the patient is apt to lie on the catheter for a prolonged period of time.

Preferably, the relatively soft distal end portion and the relatively long and rigid portion are joined together by heat and pressure sufficient to form an intermediate section or transition zone, perhaps about one-sixteenth of an inch in length in which the relatively stiff resin and the relatively soft resin interface, forming a strong bond over a relatively large surface area, which will not separate during the relatively long time that the catheter may remain in place.

In order to properly position the distal tip of the catheter within the space, and to insure that no part of the more rigid, relatively long section does not enter the space, and cause trauma to delicate tissue, it is preferred that the catheter be provided with spaced apart reference marks to visually indicate the location of the tip. For example, a first reference mark 15 is located on the catheter body so that when it is adjacent the hub of the needle, it will indicate to the anesthesiologist that the tip of the catheter coincides with the tip of the needle. A second marking 16, spaced proximally from the first by the insertion length of the soft distal end section, will indicate to the user that the approximate length of the distal end of the catheter has been inserted into the space when the second marking 16 is adjacent the hub. Additional markings intermediate the first two markings may be provided if desired.

Figure 2:
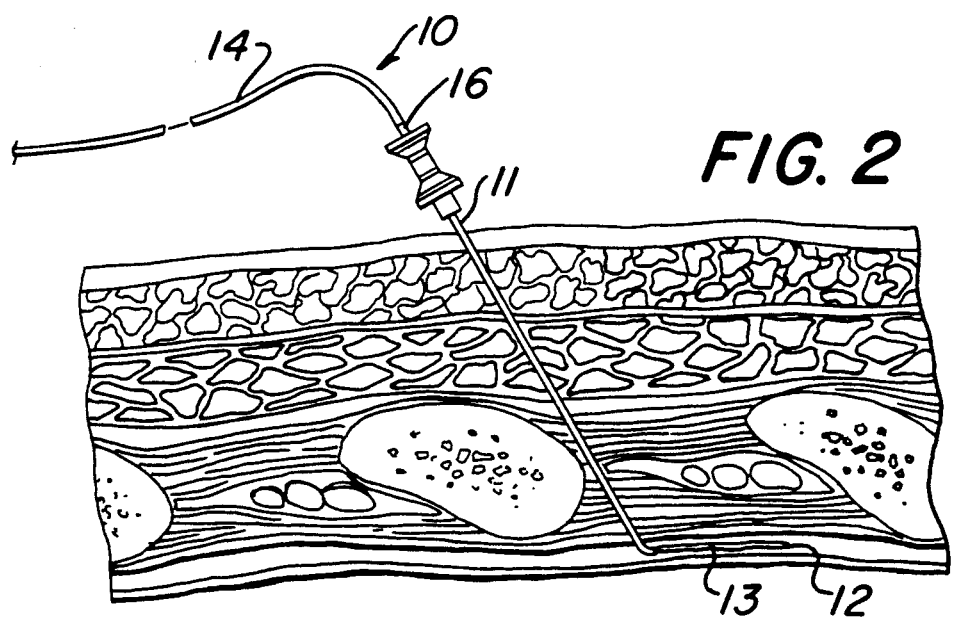
FIG. 2 shows the catheter of FIG. 1 fully advanced to the appropriate position within the pleural space.
Figure 3:
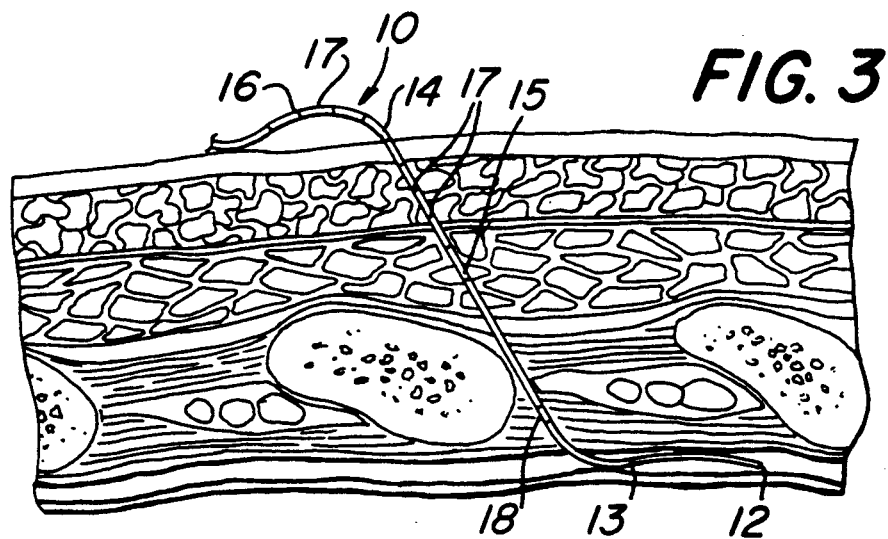
FIG. 3 shows the catheter ready for use with the needle removed.

In use of the catheter in the administration of the anesthetic in the intra-pleural space, a curved-tip needle 11 is inserted at the chosen intercostal space as seen in FIG. 1. Once the needle tip is properly positioned within the space, the catheter is threaded through the needle hub and advanced until the first reference mark 15 reaches the hub of the needle. This will indicate that the distal tip of the catheter is about to exit from the needle tip. The user should experience less resistance once the catheter exits from the needle tip and is advanced into the intrapleural space. Once the marking 16 is adjacent the needle hub, as seen in FIG. 2, the appropriate amount of soft catheter is within the pleural space, no further advancement should be attempted as to avoid any risk that the relatively rigid catheter material may be entering the space. At this point the needle is removed and separated from the catheter as seen in FIG. 3.

We claim:

1. Equipment for administration of fluids, such as an anesthetic or the like, into an elongated body space having a relatively narrow clear space in the direction of access thereto, said equipment comprising a catheter having a first elongated body portion extending proximally from the distal tip and a second elongated body portion extending proximally of said first body portion and joined thereto, said first body portion being formed of a relatively soft bio-compatible resin material and said second portion being of relatively stiff bio-compatible resin material, a lumen extending lengthwise of the catheter having an exit port in said first body portion in the region of the distal tip, the exterior of said second body portion having a reference means for indicating the position of the distal tip of the catheter within the elongated body space, the material of said first body portion being yieldable upon contact with body tissue within said space without irritation thereto and the material of said second body portion being resistant to collapse and kinking, said reference means comprising a plurality of reference marks disposed on said second body portion, the first of said reference marks being offset from the distal tip of the catheter by an amount equal to the length of an insertion needle used in placement of the catheter and a second of said reference marks placed proximally of the first by an amount equivalent to the insertion length of said first body portion within said body space.

2. Equipment according to claim 8 wherein said first body portion is formed of a material having a durometer reading of between about 80A and 100A Shore.

3. Equipment according to claim 2 wherein the material of said first body portion has a durometer reading of about 93A Shore.

4. Equipment according to claim 2 wherein the second body portion has a durometer reading of about 65D to about 75D Shore.

5. Equipment according to claim 4 wherein the material of said second body portion has a durometer reading of about 68D Shore.

6. Equipment according to claim 1 wherein said first body portion consists essentially of polyurethane.

7. Equipment according to claim 6 wherein said second body portion consists of polyurethane.

8. Equipment according to claim 7 wherein said polyurethane is an aliphatic polyurethane.

9. Equipment according to claim 8 wherein the first body portion has a length of at least 5 centimeters.

10. Equipment according to claim 1 wherein said reference means comprises at least one reference mark on said second body portion in position to visually indicate the location of the distal tip within the body space.

11. A method of administering a fluid, such as an anesthetic, into a relatively elongated body space having a relatively narrow dimension in the direction of access thereto which comprises advancing a needle into the body space in a direction extending transversely of the body space, inserting a catheter into said needle, said catheter having a first elongated body portion extending proximally from the distal tip and a second elongated body portion extending proximally of said first body portion and joined thereto, said first and second body portions being of substantially uniform and equal outer diameter, said first body portion being formed of a relatively soft material and said second portion being of relatively stiff material, a lumen extending lengthwise of the catheter having an ext port in said first body portion in the region of the distal tip, the exterior surface of said second body portion having an indicator marking disposed proximally of the juncture of the first and second body portions, said indicator marking providing a visual indication of the tip position relative to the body space, a second indicator marking disposed proximally of the first by an amount equal to the length of the first body portion which is intended to reside within the body space, the material of said first body portion being yieldable upon contact with body tissue within said space without irritation thereto and the material of said second body portion being resistant to collapse and kinking, said method further comprising terminating advancement of the catheter into the body space before said second indicator marking enters the skin of the patient, and withdrawing said needle prior to administering said fluid into said elongated body space.

* * * * *

UNITED STATES PATENT AND TRADEMARK OFFICE
CERTIFICATE OF CORRECTION

PATENT NO. : 5,004,456
DATED : April 2, 1991
INVENTOR(S) : Carl N. Botterbusch & Paul L. Frankhouser It is certified that error appears in the above-identified patent and that said Letters Patent is hereby corrected as shown below: Title Page:

In the Abstract, lines 10 and 13, --Rockwell-- should be "Shore"

In the Claims, Column 6, line 15 of Claim 11, --ext-- should be "exit"

Column 1, line 38, --relativelY-- should be "relatively"

Column 1, line 52, --kinkresistant-- should be "kink-resistant"

Column 2, line 15, --approximatelY-- should be "approximately"

Column 2, line 23, --Rockwell-- should be "Shore"

Column 3, lines 23, 43, 47, 49 and 50, --biocompatible-- should be "bio-compatible"

Column 3, lines 48 and 56, --Rockwell-- should be "Shore"

Column 4, line 1, --pclYurethane-- should be "polyurethane"

Column 4, lines 4 and 10, --Rockwell-- should be "Shore"

Column 4, line 8, --bodY-- should be "body"

Signed and Sealed this

Sixth Day of October, 1992

Attest:

DOUGLAS B. COMER

Attesting Officer

Acting Commissioner of Patents and Trademarks